(12) United States Patent
Rath et al.

(10) Patent No.: US 7,396,531 B2
(45) Date of Patent: Jul. 8, 2008

(54) PREVENTIVE AND THERAPEUTIC USE OF POLYPEPTIDES FROM AFRICAN SWINE VIRUS AS VACCINES

(76) Inventors: Matthias Rath, Dr. Rath Health Programs B.V., Sourethweg 9 6422PC, Heerlen (NL); Aleksandra Niedzwiecki, 1354 Heckvan Way, San Jose, CA (US) 56138

( * ) Notice: Subject to any disclaimer, the term of this patent is extended or adjusted under 35 U.S.C. 154(b) by 0 days.

(21) Appl. No.: 11/481,535

(22) Filed: Jul. 5, 2006

(65) Prior Publication Data

US 2008/0008721 A1     Jan. 10, 2008

(51) Int. Cl.
*A61K 39/12*     (2006.01)
*A61K 39/00*     (2006.01)
*A61K 39/385*     (2006.01)

(52) U.S. Cl. ............... 424/186.1; 424/185.1; 424/204.1; 424/194.1

(58) Field of Classification Search ........................ None
See application file for complete search history.

(56) References Cited

U.S. PATENT DOCUMENTS 5,880,095 A  *  3/1999  Park et al. ..................... 514/12

OTHER PUBLICATIONS

Neilan et al., Neutralizing antibodies to African swine fever virus proteins p30, p54 and p72 are not sufficient for antibody-mediated protection, 2004, Virology, vol. 319, pp. 337-342.*
Simon-Mateo et al., Polyprotien processing in African swine fever virus: a novel gene express strategy for a DNA virus, 1993, The EMBO Journal, vol. 12, No. 7, pp. 2977-2987.*
Genbank Accession #CAA80455, African Swine Fever Virus Polyprotein 220, Accessioned Apr. 29, 1995.*

* cited by examiner

*Primary Examiner*—Bruce Campell
*Assistant Examiner*—Benjamin P. Blumel
(74) *Attorney, Agent, or Firm*—Ali Kamarei, Esq.; Alexander Chen, Esq.

(57) ABSTRACT

The present invention relates to the use of selected polypeptides from African Swine virus for the prevention and therapy of African Swine infections as well as other infections, including immune deficiencies in mammals and humans.

2 Claims, 1 Drawing Sheet

SEQUENCE LISTING

<160> NUMBER OF SEQ ID NOS: 111

<210> SEQ ID NO 1
<211> LENGTH: 26
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 1

```
Ser Arg Pro Pro Leu Ser Ser Glu Ala Asn Leu Tyr Ala Lys Leu Gln
1               5                   10                  15

Asp His Ile Gln Arg Gln Thr Arg Pro Phe
            20                  25

<210> SEQ ID NO 2
<211> LENGTH: 16
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 2

Gly Asp Lys Asn Pro Val Gln His Ile Lys Asp Tyr His Ile Asp Ser
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 3

Ser Lys Ala Lys Leu Arg Val Ile Glu Gly Ile Ile Arg Ala
1               5                   10

<210> SEQ ID NO 4
<211> LENGTH: 25
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 4

Phe Lys Val Asp Thr Lys Gln Pro Ile Glu Asp Ile Leu Lys Asp Ile
1               5                   10                  15

Lys Lys Gln Leu Pro Asp Pro Arg Ala
            20                  25

<210> SEQ ID NO 5
<211> LENGTH: 10
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 5

Ala Glu Lys Gln Glu Thr Val Cys Lys Met
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 6

Gln Glu Phe Ile Asp Leu Gly Gln Asp Lys Leu Ile Asp Thr
1               5                   10
```

```
<210> SEQ ID NO 7
<211> LENGTH: 40
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 7

Ala Glu Lys Gln Glu Thr Val Cys Lys Met Ile Ala Asp Ala Ile Asn
1               5                   10                  15

Gln Glu Phe Ile Asp Leu Gly Gln Asp Lys Leu Ile Asp Thr Thr Asp
            20                  25                  30

Gly Ala Ala Ser Ile Cys Arg Gln
        35                  40

<210> SEQ ID NO 8
<211> LENGTH: 21
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 8

Leu Arg Ala Glu Tyr Leu Asp Val His Gly Ser Ile Glu Asn Thr Leu
1               5                   10                  15

Glu Asn Ile Lys Leu
            20

<210> SEQ ID NO 9
<211> LENGTH: 12
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 9

Asn Asp Ala Ile Lys Gln Leu His Glu Arg Met Val
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 10

Thr Glu Val Thr Lys Ala Ala Pro Asn Glu Glu Val
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 11

Ile Glu Ala Val Tyr Arg Arg Leu Leu Asn Glu Gln Asn Leu
1               5                   10
```

```
<210> SEQ ID NO 12
<211> LENGTH: 15
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 12

Thr Gln Lys Glu Leu Asp Lys Leu Gln Thr Asp Glu Val Asp Ile
1               5                   10                  15

<210> SEQ ID NO 13
<211> LENGTH: 81
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 13

Leu Cys Asn Leu Gly Ile Ala Ala Ser Val Ala Asn Lys Ile Asn Lys
1               5                   10                  15

Ala Leu Gln Lys Val Gly Leu Lys Val Glu Gln Tyr Leu Gln Ser Lys
            20                  25                  30

Asn Trp Ala Glu Phe Asp Lys Glu Leu Asp Leu Lys Arg Phe Ser Gly
        35                  40                  45

Leu Val Ser Ala Glu Asn Ile Ala Glu Phe Glu Lys Ala Val Asn Leu
    50                  55                  60

Leu Arg Gln Thr Phe Asn Glu Arg His Lys Ile Leu Glu Asn Ser Cys
65                  70                  75                  80

Ala

<210> SEQ ID NO 14
<211> LENGTH: 14
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 14

Asn Lys Ile Asn Lys Ala Leu Gln Lys Val Gly Leu Lys Val
1               5                   10

<210> SEQ ID NO 15
<211> LENGTH: 16
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 15

Ser Lys Asn Trp Ala Glu Phe Asp Lys Glu Leu Asp Leu Lys Arg Phe
1               5                   10                  15

<210> SEQ ID NO 16
<211> LENGTH: 27
<212> TYPE: PRT
<213> ORGANISM: Artificial Sequence
<220> FEATURE:
<223> OTHER INFORMATION: Polypeptides from African Swine Virus
      as vaccines for preventive and therapeutic use
```

```
<400> SEQUENCE: 16

Ala Glu Asn Ile Ala Glu Phe Glu Lys Ala Val Asn Leu Leu Arg Gln
1               5                   10                  15

Thr Phe Asn Glu Arg His Lys Ile Leu Glu Asn
            20                  25

<210> SEQ ID NO 17
<211> LENGTH: 10
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 17

Ala Lys Lys Gly Gly Asp Glu Glu Lys Thr
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 18

Pro Leu Asp Arg Arg Ile Glu Ala Gln Arg Leu Asp Arg Lys His Ile
1               5                   10                  15

<210> SEQ ID NO 19
<211> LENGTH: 26
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 19

Ala Lys Lys Gly Gly Asp Glu Glu Lys Thr Pro Leu Asp Arg Arg Ile
1               5                   10                  15

Glu Ala Gln Arg Leu Asp Arg Lys His Glu
            20                  25

<210> SEQ ID NO 20
<211> LENGTH: 18
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 20

Asn Asp Phe Leu Glu Asn Val Lys Lys Ile Gly Ile Lys Leu Val Lys
1               5                   10                  15

Glu Ile

<210> SEQ ID NO 21
<211> LENGTH: 13
<212> TYPE: PRT
<213> ORGANISM: Artificial Sequence
<220> FEATURE:
<223> OTHER INFORMATION: Polypeptides from African Swine Virus
      as vaccines for preventive and therapeutic use
```

```
<400> SEQUENCE: 21

Thr Arg Leu Arg Asp Ala Leu Ser Arg Ile Asn Asp Met
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 22

Ala Arg Glu Glu Arg Glu Thr Phe
1               5

<210> SEQ ID NO 23
<211> LENGTH: 17
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 23

Val Lys Asn Val Leu Glu Glu Gln Ser Lys Ile Asp Pro Asn Phe Lys
1               5                   10                  15

Asn

<210> SEQ ID NO 24
<211> LENGTH: 33
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 24

Tyr Asp Ser Cys Ser Arg Leu Leu Gln Ile Ile Asp Phe Tyr Thr Asp
1               5                   10                  15

Ile Val Gln Lys Lys Tyr Gly Gly Gly Glu Asp Cys Glu Cys Thr Arg
            20                  25                  30

Val

<210> SEQ ID NO 25
<211> LENGTH: 29
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 25

Tyr Asp Ser Cys Ser Arg Leu Leu Gln Ile Ile Asp Phe Tyr Thr Asp
1               5                   10                  15

Ile Val Gln Lys Lys Tyr Gly Gly Gly Glu Asp Cys Glu
            20                  25

<210> SEQ ID NO 26
<211> LENGTH: 16
<212> TYPE: PRT
<213> ORGANISM: Artificial Sequence
<220> FEATURE:
<223> OTHER INFORMATION: Polypeptides from African Swine Virus
      as vaccines for preventive and therapeutic use
```

```
<400> SEQUENCE: 26

Val Gln Lys Lys Tyr Gly Gly Gly Glu Asp Cys Glu Cys Thr Arg Val
1               5                   10                  15

<210> SEQ ID NO 27
<211> LENGTH: 49
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 27

Val Glu Glu Leu Gly Leu Ser Lys Ala Ala Arg Ser Gln Val Asp Leu
1               5                   10                  15

Asn Gln Ala Ile Asn Thr Phe Met Tyr Tyr Tyr Val Ala Gln Ile
            20                  25                  30

Tyr Ser Asn Leu Thr His Asn Lys Gln Glu Phe Gln Ser Tyr Glu Glu
        35                  40                  45

Asn

<210> SEQ ID NO 28
<211> LENGTH: 13
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 28

Thr His Asn Lys Gln Glu Phe Gln Ser Tyr Glu Glu Asn
1               5                   10

<210> SEQ ID NO 29
<211> LENGTH: 21
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 29

Met Gln Leu Asp Thr Glu Lys Asn Ala Arg Ile Asn Ser Pro Ala Val
1               5                   10                  15

Asp Leu Ala Arg Gly
            20

<210> SEQ ID NO 30
<211> LENGTH: 32
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 30

Ala Gln Glu Ala Asp Trp Lys Ala Ala Val Ser Ala Ile Glu Leu Glu
1               5                   10                  15

Tyr Asp Val Lys Arg Arg Phe Tyr Arg Ala Leu Glu Gly Leu Asp Leu
            20                  25                  30

<210> SEQ ID NO 31
<211> LENGTH: 14
```

```
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 31

Leu Lys Asn Ile Thr Lys Thr Phe Val Asn Asn Ile Asp Ser
1               5                   10

<210> SEQ ID NO 32
<211> LENGTH: 18
<212> TYPE: PRT
<213> ORGANISM: Artificial Sequence
<220> FEATURE:
<223> OTHER INFORMATION: Polypeptides from African Swine Virus as
      vaccines for preventive and therapeutic use

<400> SEQUENCE: 32

Leu Asp Gly Val Arg Ile Ile Gly Arg Trp Phe Thr Glu Ala Thr Gly
1               5                   10                  15

Asp Thr

<210> SEQ ID NO 33
<211> LENGTH: 26
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 33

Ala Glu Ile Gln Gln Gly Arg Ser Val Gly Thr Leu Arg Pro Val Arg
1               5                   10                  15

Ala Ser Gln Ala Lys Asn Ile Arg Asp Leu
            20                  25

<210> SEQ ID NO 34
<211> LENGTH: 15
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 34

Ala Arg Ile Gly Asp Met Leu Gly Gly Glu Glu Leu Arg Gln Met
1               5                   10                  15

<210> SEQ ID NO 35
<211> LENGTH: 27
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 35

Leu Lys Asn Leu Asn Gln Ser Glu Ile Gly Gly Gln Arg Val Ala Leu
1               5                   10                  15

Ala Arg Thr Pro Glu Glu Ala Ala Gln Arg Val
            20                  25

<210> SEQ ID NO 36
<211> LENGTH: 13
<212> TYPE: PRT
```

<213> ORGANISM: Artificial Sequence
<220> FEATURE:
<223> OTHER INFORMATION: Polypeptides from African Swine Virus
      as vaccines for preventive and therapeutic use

<400> SEQUENCE: 36

Asn Asp Ala Leu Ser Thr Arg Trp Glu Thr Glu Asp Val
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 37

Tyr Asp Met Phe Glu Arg Pro Glu Pro Val Tyr Lys Leu
1               5                   10

<210> SEQ ID NO 38
<211> LENGTH: 22
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 38

Ala Asp Glu Leu Glu Pro Glu Val Ile Pro Glu Ala Ala Glu Leu Tyr
1               5                   10                  15

Phe Arg Leu Pro Arg Leu
            20

<210> SEQ ID NO 39
<211> LENGTH: 13
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 39

Phe Arg Leu Pro Arg Leu Ala Glu Phe Tyr Gln Lys Leu
1               5                   10

<210> SEQ ID NO 40
<211> LENGTH: 24
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 40

Met Arg Pro Ile Glu Leu Ile Asn Ile Gly Asp Tyr Ser Glu Thr Glu
1               5                   10                  15

Ile Arg Gln Leu Ile Lys Glu Ile
            20

<210> SEQ ID NO 41
<211> LENGTH: 20
<212> TYPE: PRT
<213> ORGANISM: Artificial Sequence
<220> FEATURE:
<223> OTHER INFORMATION: Polypeptides from African Swine Virus -continued as vaccines for preventive and therapeutic use

<400> SEQUENCE: 41

Leu Glu Tyr Gly Glu Gln Glu Ala Thr Lys Lys Ala Leu Ile His Phe
1               5                   10                  15

Val Asn Glu Ile
            20

<210> SEQ ID NO 42
<211> LENGTH: 18
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 42

Asn Arg Arg Phe Gly Val Ile Thr Arg Thr Glu Trp Glu Lys Phe Gln
1               5                   10                  15

Arg Ile

<210> SEQ ID NO 43
<211> LENGTH: 14
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 43

Gln Arg Ile Val Gln Glu Ala Arg Thr Met Asn Asp Phe Gly
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 44

Ser Gln Trp Asp Leu Val Gln Lys Phe Arg Lys Gln Leu
1               5                   10

<210> SEQ ID NO 45
<211> LENGTH: 15
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 45

Gln Lys Phe Arg Lys Gln Leu Ser Glu Met Phe Glu Asp Pro Ser
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 46

```
Gln Gln Glu Leu Gly Lys Val Ser Tyr Gln Glu Leu Ile Arg Gln
1               5                   10                  15

<210> SEQ ID NO 47
<211> LENGTH: 18
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 47

Ile Asn Glu Leu Lys Lys Glu His Thr Asp Lys Ile Gln Ile Val Ser
1               5                   10                  15

Lys Leu

<210> SEQ ID NO 48
<211> LENGTH: 30
<212> TYPE: PRT
<213> ORGANISM: Artificial Sequence
<220> FEATURE:
<223> OTHER INFORMATION: Polypeptides from African Swine Virus
      vaccines for preventive and therapeutic use

<400> SEQUENCE: 48

Leu Lys Lys Glu His Thr Asp Lys Ile Gln Ile Val Ser Lys Leu Ile
1               5                   10                  15

Gln Gly Ser Glu Ser Leu Ala Asp Thr Asp Val Asn Lys Ile
            20                  25                  30

<210> SEQ ID NO 49
<211> LENGTH: 16
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 49

Phe Arg Asn Asn Ile Lys Gly Leu Asp Leu Asp Thr Ile Gln Lys Ser
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 50

Ile Glu Trp Leu Arg Glu Thr Gln Ala Ala Asn Val Asn Arg Ala
1               5                   10                  15

<210> SEQ ID NO 51
<211> LENGTH: 14
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 51

Ile Asp Trp Leu Gly Arg Lys His Gly Ala Ile Ser Glu Ile
1               5                   10
```

```
<210> SEQ ID NO 52
<211> LENGTH: 18
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 52

Ile Arg Asn Pro Gly Leu Val Val Lys Glu Asn Asp Val Arg Leu Ser
1               5                   10                  15

Arg Val

<210> SEQ ID NO 53
<211> LENGTH: 16
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 53

Ala Glu Gln Glu Leu Ala Ala Arg Tyr Leu Val Asp Asn Gln Arg Ile
1               5                   10                  15

<210> SEQ ID NO 54
<211> LENGTH: 12
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 54

Phe Asn Lys Met Val Gln Val Arg Phe Pro Glu Thr
1               5                   10

<210> SEQ ID NO 55
<211> LENGTH: 22
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 55

Ile Asp Ser Leu Met Ala Asp Thr Lys Tyr Phe Leu Asn Leu Leu Arg
1               5                   10                  15

Pro His Ile Asp Lys Asn
            20

<210> SEQ ID NO 56
<211> LENGTH: 16
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 56

Leu Glu Glu His Leu Ile Asp Lys Leu Ile Lys Pro Pro Thr Asp Ala
1               5                   10                  15

<210> SEQ ID NO 57
<211> LENGTH: 12
<212> TYPE: PRT
<213> ORGANISM: Artificial Sequence
```

-continued

```
<220> FEATURE:
<223> OTHER INFORMATION: Polypeptides from African Swine Virus
      as vaccines for preventive and therapeutic use

<400> SEQUENCE: 57

Leu Gln Leu Arg Gly Gly Val Gln Arg Arg Asp Ala
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 58

Ser Glu Arg Phe Glu Gln Tyr Gly Arg Val
1               5                   10

<210> SEQ ID NO 59
<211> LENGTH: 33
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 59

Leu Gln Leu Arg Gly Gly Val Gln Arg Arg Asp Ala Ala Asn Ile Gln
1               5                   10                  15

Ile Asn Asn Asn Pro Gln Pro Ser Glu Arg Phe Glu Gln Tyr Gly Arg
            20                  25                  30

Val

<210> SEQ ID NO 60
<211> LENGTH: 11
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 60

Ile Arg Thr Asn Asn Ala Gln Glu Glu Asn Thr
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 61

Leu Arg Arg Tyr Arg Leu Tyr Gly Ser Asp Tyr
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Polypeptides from African Swine Virus
      as vaccines for preventive and therapeutic use
```

-continued

```
<400> SEQUENCE: 62

Ala Arg Phe Tyr Asp Ala Pro Ser Gly Lys Ile
1               5                   10

<210> SEQ ID NO 63
<211> LENGTH: 27
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 63

Met Glu Leu Gly Tyr Thr His Pro Asp Leu Ala Arg Asp Asn Ile Ala
1               5                   10                  15

Phe Gly His Arg Gly Asp Pro Thr Glu Gln Ser
            20                  25

<210> SEQ ID NO 64
<211> LENGTH: 12
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 64

Leu Gln Arg Leu Ile Lys Asp Thr Asn Arg Gln Gly
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 65

Thr Glu Ile Pro Ile Tyr Leu Lys Glu Asn Tyr Arg Ala
1               5                   10

<210> SEQ ID NO 66
<211> LENGTH: 34
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 66

Leu Gln Arg Leu Ile Lys Asp Thr Asn Arg Gln Gly Leu Ser Gln His
1               5                   10                  15

Leu Ile Ser Thr Leu Thr Glu Ile Pro Ile Tyr Leu Lys Glu Asn Tyr
            20                  25                  30

Arg Ala

<210> SEQ ID NO 67
<211> LENGTH: 18
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 67
```

```
Ser Asp Val Val Arg Lys Arg Leu Val Ala Val Ile Asp Gly Ile Ile
1               5                   10                  15

Arg Gly

<210> SEQ ID NO 68
<211> LENGTH: 20
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 68

Tyr Leu Glu Thr Glu Glu His Phe Ile Gln Asn Tyr Met Ser Arg Tyr
1               5                   10                  15

Asn Lys Glu Pro
            20

<210> SEQ ID NO 69
<211> LENGTH: 16
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 69

Tyr Leu Arg Asp Leu Arg Ile Glu Asn Asn Glu Val Tyr Asp Pro Leu
1               5                   10                  15

<210> SEQ ID NO 70
<211> LENGTH: 17
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 70

Leu Glu Ser Gly Ser Pro Glu Phe Lys Leu Leu Tyr Gly Thr Arg Lys
1               5                   10                  15

Leu

<210> SEQ ID NO 71
<211> LENGTH: 21
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 71

Met Lys Asn Tyr Asn Glu Thr Val Val Ala Arg Glu Gln Ile Thr Pro
1               5                   10                  15

Thr Arg Phe Glu His
            20

<210> SEQ ID NO 72
<211> LENGTH: 10
<212> TYPE: PRT
<213> ORGANISM: Artificial Sequence
<220> FEATURE:
<223> OTHER INFORMATION: Polypeptides from African Swine Virus
      as vaccines for preventive and therapeutic use
```

```
<400> SEQUENCE: 72

Ile Ser Glu Asn Arg Asp Asp Lys Pro Ile
1               5                   10

<210> SEQ ID NO 73
<211> LENGTH: 27
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 73

Leu Arg Lys Thr Leu Gln Asp Val Ile Ser Phe Val Glu Ser Ser Tyr
1               5                   10                  15

Gln Glu Glu Gln Ile Asn His Ile His Lys Ile
            20                  25

<210> SEQ ID NO 74
<211> LENGTH: 17
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 74

Pro Lys Gly Gln Thr Arg Thr Leu Gly Ser Asn Arg Glu Arg Glu Arg
1               5                   10                  15

Ile

<210> SEQ ID NO 75
<211> LENGTH: 22
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 75

Tyr Asp Tyr Ser Phe Glu Glu Ile Ala Cys Leu Met Tyr Gly Ile Ser
1               5                   10                  15

Ala Glu Lys Val Arg Ser
            20

<210> SEQ ID NO 76
<211> LENGTH: 24
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 76

Pro Asp Ile Ala Glu Val Leu Asn Ile Pro Asn Arg Pro Pro Met Asn
1               5                   10                  15

Thr Arg Glu Phe Met Leu Lys Leu
            20

<210> SEQ ID NO 77
<211> LENGTH: 27
<212> TYPE: PRT
<213> ORGANISM: Artificial Sequence
<220> FEATURE:
<223> OTHER INFORMATION: Polypeptides from African Swine Virus
``` as vaccines for preventive and therapeutic use

<400> SEQUENCE: 77

Met Ser Arg Ile Phe Arg Gly Asp Asn Ala Leu Asn Met Gly Arg Pro
1               5                   10                  15

Lys Phe Leu Ser Asp Gln Ile Phe Asn Lys Val
            20                  25

<210> SEQ ID NO 78
<211> LENGTH: 9
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 78

Ile Gln Arg Gly Arg Glu Gln Trp Gly
1               5

<210> SEQ ID NO 79
<211> LENGTH: 25
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 79

Glu Tyr Ile Asn Gln Ala Leu His Glu Leu Val Arg Thr Ile Arg Ile
1               5                   10                  15

Pro Gln Lys Leu Arg Val Leu Arg Asn
            20                  25

<210> SEQ ID NO 80
<211> LENGTH: 27
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 80

Ile Arg Glu Gln Leu Val Ser Met Arg Arg Glu Val Glu Asn Met Ile
1               5                   10                  15

Gln Thr Pro Glu Ile Gln Asn Asn Pro Thr Pro
            20                  25

<210> SEQ ID NO 81
<211> LENGTH: 10
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 81

Thr Gln Gln Tyr Arg Ala Arg Val Asp Thr
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Polypeptides from African Swine Virus as vaccines for preventive and therapeutic use

<400> SEQUENCE: 82

His Pro Arg Gln Ile Leu Gln Thr Asp Asp Glu Ala
1               5                   10

<210> SEQ ID NO 83
<211> LENGTH: 17
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 83

Thr Asp Leu Ala Asn Asp Leu Arg Thr Phe Leu Glu Thr Leu Glu Arg
1               5                   10                  15

Tyr

<210> SEQ ID NO 84
<211> LENGTH: 19
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 84

Gly Arg Val Ala Arg Ala Pro Val Arg Met Ala Pro Arg Asp Met Arg
1               5                   10                  15

His Pro Ile

<210> SEQ ID NO 85
<211> LENGTH: 48
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 85

Thr Asp Leu Ala Asn Asp Leu Arg Thr Phe Leu Glu Thr Leu Glu Arg
1               5                   10                  15

Tyr Val Phe Asn Val Pro Arg Trp Leu Gly Pro Ser Thr Gly Arg Val
                20                  25                  30

Ala Arg Ala Pro Val Arg Met Ala Pro Arg Asp Met Arg His Pro Ile
        35                  40                  45

<210> SEQ ID NO 86
<211> LENGTH: 9
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 86

Thr Glu Gln Asn Arg Glu Glu Gly Pro
1               5

<210> SEQ ID NO 87
<211> LENGTH: 37
<212> TYPE: PRT
<213> ORGANISM: Artificial Sequence
<220> FEATURE:

```
<223> OTHER INFORMATION: Polypeptides from African Swine Virus
      as vaccines for preventive and therapeutic use

<400> SEQUENCE: 87

Thr Glu Gln Asn Arg Glu Glu Gly Pro Trp Ser Ile Val Lys Gln Val
1               5                   10                  15

Gly Val Gly Ile Gln Lys Pro Thr Leu Val Gln Ile Gly Lys Asp Arg
            20                  25                  30

Phe Asp Thr Arg Leu
            35

<210> SEQ ID NO 88
<211> LENGTH: 9
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 88

Gly Lys Asp Arg Phe Asp Thr Arg Leu
1               5

<210> SEQ ID NO 89
<211> LENGTH: 18
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 89

Ile Gln Arg Leu Leu Arg Leu Arg Leu Asn Leu Glu Leu Ser Gln Phe
1               5                   10                  15

Arg Asn

<210> SEQ ID NO 90
<211> LENGTH: 15
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 90

Val Gln Ile Gly Lys Asp Arg Phe Asp Thr Arg Leu Ile Arg Asn
1               5                   10                  15

<210> SEQ ID NO 91
<211> LENGTH: 18
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 91

Ile Gln Arg Leu Leu Arg Leu Arg Leu Asn Leu Glu Leu Ser Gln Phe
1               5                   10                  15

Arg Asn

<210> SEQ ID NO 92
<211> LENGTH: 15
<212> TYPE: PRT
<213> ORGANISM: Artificial Sequence
```

```
<220> FEATURE:
<223> OTHER INFORMATION: Polypeptides from African Swine Virus
      as vaccines for preventive and therapeutic use

<400> SEQUENCE: 92

Ser Glu Thr Phe Ser Asp Lys Gln Tyr Asp Ser Asp Ile Arg Ile
1               5                   10                  15

<210> SEQ ID NO 93
<211> LENGTH: 14
<212> TYPE: PRT
<213> ORGANISM: Artificial Sequence
<220> FEATURE:
<223> OTHER INFORMATION: Polypeptides from African Swine Virus
      vaccines for preventive and therapeutic use

<400> SEQUENCE: 93

Trp Glu Ser Asp Leu Pro Arg His Asn Arg Tyr Ser Asp Asn
1               5                   10

<210> SEQ ID NO 94
<211> LENGTH: 21
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 94

Asn Glu Tyr Thr Asn Ser Pro Glu Lys Ala Glu Lys Gly Leu Gln Leu
1               5                   10                  15

Ser Asp Leu Arg Asn
            20

<210> SEQ ID NO 95
<211> LENGTH: 16
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 95

Gln His Lys Asn Ile Gly Tyr Gly Asp Ala Gln Asp Leu Glu Pro Tyr
1               5                   10                  15

<210> SEQ ID NO 96
<211> LENGTH: 17
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 96

Gly Asp Ala Gln Asp Leu Glu Pro Tyr Ser Ser Ile Pro Lys Asn Lys
1               5                   10                  15

Leu

<210> SEQ ID NO 97
<211> LENGTH: 16
<212> TYPE: PRT
<213> ORGANISM: Artificial Sequence
<220> FEATURE:
<223> OTHER INFORMATION: Polypeptides from African Swine Virus
      as vaccines for preventive and therapeutic use
```

-continued

```
<400> SEQUENCE: 97

Thr Glu Asn Leu Ile Arg Arg Asn Val Val Arg Thr Glu Lys Lys Thr
1               5                   10                  15

<210> SEQ ID NO 98
<211> LENGTH: 9
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 98

Thr Arg Phe Ser Glu His Thr Lys Phe
1               5

<210> SEQ ID NO 99
<211> LENGTH: 19
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 99

Tyr Glu Asp Ile Pro Lys Leu Lys Thr Lys Gly Thr Ile Lys His Glu
1               5                   10                  15

Gln His Leu

<210> SEQ ID NO 100
<211> LENGTH: 9
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 100

Val Glu Lys Gly Ile Ala Gly Arg Gly
1               5

<210> SEQ ID NO 101
<211> LENGTH: 12
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 101

Val Lys Pro Asn Ile Glu Gln Glu Leu Ile Lys Ser
1               5                   10

<210> SEQ ID NO 102
<211> LENGTH: 28
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 102

Val Glu Lys Gly Ile Ala Gly Arg Gly Ile Pro Leu Gly Asn Pro His
1               5                   10                  15

Val Lys Pro Asn Ile Glu Gln Glu Leu Ile Lys Ser
            20                  25
```

<210> SEQ ID NO 103
<211> LENGTH: 18
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 103

```
Pro Lys Asp Ser Gln His Gly Arg Glu Tyr Gln Glu Phe Ser Ala Asn
1               5                   10                  15

Arg His
```

<210> SEQ ID NO 104
<211> LENGTH: 9
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 104

```
Ile Lys Pro Gln Ile Leu Glu Asp Ile
1               5
```

<210> SEQ ID NO 105
<211> LENGTH: 16
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 105

```
Ser Lys Arg Asn Ser Gly Gln Ala Glu Tyr Phe Asp Thr Ser Lys Gln
1               5                   10                  15
```

<210> SEQ ID NO 106
<211> LENGTH: 12
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 106

```
Gly Asp Ser Lys Leu Asp Ser Thr Phe Pro Lys Asp
1               5                   10
```

<210> SEQ ID NO 107
<211> LENGTH: 11
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 107

```
Ala Glu Lys Asp His Ser Leu Arg Gly Asp Asn
1               5                   10
```

<210> SEQ ID NO 108
<211> LENGTH: 66
<212> TYPE: PRT
<213> ORGANISM: Artificial Sequence
<220> FEATURE:

```
-continued

<223> OTHER INFORMATION: Polypeptides from African Swine Virus
      as vaccines for preventive and therapeutic use

<400> SEQUENCE: 108

Ser Ala Glu Lys Asp His Ser Leu Arg Gly Asp Asn Ser Ala Cys Cys
1               5                   10                  15

Ile Ser Asn Tyr Ile Pro Lys Tyr Thr Gly Ile Gly Asp Ser Lys
            20                  25                  30

Leu Asp Ser Thr Phe Pro Lys Asp Phe Asn Ala Ser Val Pro Leu
        35                  40                  45

Thr Ser Ala Glu Lys Asp His Ser Leu Arg Gly Asp Asn Ser Ala Cys
    50                  55                  60

Cys Ile
65

<210> SEQ ID NO 109
<211> LENGTH: 13
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 109

Gly Asp Ser Lys Leu Asp Ser Thr Phe Pro Lys Asp Phe
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 110

Ala Glu Lys Asp His Ser Leu Arg Gly Asp Asn
1               5                   10

<210> SEQ ID NO 111
<211> LENGTH: 33
<212> TYPE: PRT
<213> ORGANISM: Artificial Sequence
<220> FEATURE:
<223> OTHER INFORMATION: Polypeptides from African Swine Virus
      as vaccines for preventive and therapeutic use

<400> SEQUENCE: 111

Gly Asp Ser Lys Leu Asp Ser Thr Phe Pro Lys Asp Phe Asn Ala Ser
1               5                   10                  15

Ser Val Pro Leu Thr Ser Ala Glu Lys Asp His Ser Leu Arg Gly Asp
            20                  25                  30

Asn
```

PREVENTIVE AND THERAPEUTIC USE OF POLYPEPTIDES FROM AFRICAN SWINE VIRUS AS VACCINES

FIELD OF THE INVENTION

The present invention generally relates to the use of selected polypeptides from African Swine virus for the prevention and therapy of African Swine infections as well as other infections, including immune deficiencies in mammals and humans.

BACKGROUND OF THE INVENTION

African Swine fever is an endemic disease in sub-Saharan Africa and many other parts of the developing world. It is caused by the African Swine virus that primarily replicates in macrophages and monocytes leading to the impairment of the structure and function of the immune system of the infected organisms. Until now the African Swine epidemic continues to spread despite all efforts to contain it. Thus, there is an objective need for effective, safe and affordable preventive and therapeutic approaches, in particular for effective vaccines, to control and eventually eradicate this disease.

Since the characteristic feature of the African Swine virus is to impair the immune system and to cause immune deficiencies in its hosts the development of vaccines and other therapeutic approaches against the African Swine virus has implications for other immune deficiencies or diseases. Several other viruses are also known to cause immunodeficiency-like syndromes in humans, including cytomegalovirus, Epstein Barr Virus and others. Moreover, a series of cases of so-called "idiopathic" immunodeficiencies have been documented that display CD4+ T-lymphocytopenia with opportunistic infections, but show no evidence of HIV infection (1).

Since antibodies for the African Swine virus have been detected in humans, the possibility of human infection with the African Swine virus exists and may thus far have escaped any systematic screening. Thus, any preventive and therapeutic approach to African Swine fever can have far-reaching implications to control immune deficiency conditions in humans.

SUMMARY OF THE INVENTION

Synthetic oligopeptides prepared from African Swine virus proteins are effective in prevention, treatment and diagnosis of African Swine fever as well as for immune deficiencies in humans.

Oligopeptides are identified and selected by means of suitable algorithms from the known amino acid sequence of pathogenicity-mediating African Swine virus proteins. Subsequently, these oligopeptides are tested in vitro for their ability to decrease or completely block infection by the African Swine virus (prevention and therapy) or for their ability to raise antibodies to detect the virus (diagnosis). Ultimately, the successfully tested African Swine oligopeptides can be used in veterinary and clinical medicine.

Accordingly, in one aspect, the invention provides Oligopeptides selected from the group consisting of SEQ ID NO: 1 through SEQ ID NO: 111.

In one embodiment, the oligopeptides sequences identified as SEQ ID No: 1 through SEQ ID NO: 111 are modified by omitting one or several predetermined amino residues at the N-terminal end.

In another embodiment, the oligopeptides sequences identified as SEQ ID No: 1 through SEQ ID NO: 111 are modified by omitting one or several predetermined amino acid residues at the C-terminal end.

In other embodiment, the oligopeptides sequences identified as SEQ ID No: 1 through SEQ ID NO: 111 are modified by omitting one or several predetermined amino acid residues at the N-terminal and the C-terminal end.

In yet another embodiment, the oligopeptides sequences identified as SEQ ID No: 1 through SEQ ID NO: 111 are modified by substituting one or several predetermined amino acid residues within the given sequence without consideration of charge and polarity of the substitution residue.

In still another embodiment, the oligopeptides sequences identified as SEQ ID No: 1 through SEQ ID NO: 111 are modified by substituting one or several predetermined of the amino acid residues In one embodiment, the oligopeptides sequences identified as SEQ ID No: 1 through SEQ ID NO: 111 are modified by omitting one or several predetermined amino acid residues within the given sequence.

In another embodiment, the oligopeptides sequences identified as SEQ ID No: 1 through SEQ ID NO: 111 are modified by repeating the oligopeptides sequence one or more times each of them covalently bound to one or several predetermined oligopeptides repeat(s) with linear topology or other peptidomemetic.

In yet other embodiment, the oligopeptides sequences identified as SEQ ID No: 1 through SEQ ID NO: 111 are modified by using cyclic oligopeptide topology instead of linear oligopeptide topology or other peptidomemetic.

In yet another embodiment, the oligopeptides sequences identified as SEQ ID No: 1 through SEQ ID NO: 111 are modified by repeating the oligopeptide sequence one or more times each of them covalently bound to one or more oligopeptides repeat(s) with cyclic topology or other cyclic peptidomemetic.

In still another embodiment, the oligopeptides sequences identified as SEQ ID No: 1 through SEQ ID NO: 111 that contain two residues of the amino acid cystein are modified to form disulfide bonds thereby changing the secondary and tertiary structure of the oligopeptide as well as epitope formation.

In one embodiment, modification of any of the sequences identified as SEQ ID No: 1 through SEQ ID NO: 111 by a combination of two or more of the modifications of the invention.

In another embodiment, the production of natural and/or synthetic peptidomimetics mimicking the three dimensional structure of an oligopeptide sequence according to invention and/or mimicking the three dimensional structure of a modification of such an oligopeptide according to the invention.

In one embodiment, the preventive or therapeutic use of one or more of the oligopeptides identified as SEQ ID No: 1 through SEQ ID NO: 111 and/or modifications to the invention and/or other peptidomimetics to directly and competitively reduce or block infections by the African Swine virus.

In another embodiment, the preventive or therapeutic use of one or more of the oligopeptides identified as SEQ ID No: 1 through SEQ ID NO: 111 and/or modifications to the invention and/or other peptidomimetics to indirectly reduce or block the metabolic action or interaction of African Swine virus by applying them as vaccines by subcutaneous application or in another acceptable way to stimulate a specific immune response which can partially or completely block infections by the African Swine virus.

In a preferred embodiment, the preventive or therapeutic use of one or more of the oligopeptides identified as SEQ ID No: 1 through SEQ ID NO: 111 and/or modifications to the invention and/or other peptidomimetics to directly and competitively reduce or block immune deficiencies.

In yet another preferred embodiment, the preventive or therapeutic use of one or more of the oligopeptides identified as SEQ ID No: 1 through SEQ ID NO: 111 and/or modifications to the invention and/or other peptidomimetics to indirectly reduce or block the metabolic action or interaction of African Swine virus by applying them as vaccines by subcutaneous application or in another acceptable way to stimulate a specific immune response which can partially or completely block immune deficiencies.

In still yet another preferred embodiment, the use of one or more of the oligopeptides identified as SEQ ID No: 1 through SEQ ID NO: 111 and/or modifications to the invention to prevent or treat immune deficiencies in any other medically acceptable way.

In one aspect of the invention, the use of one or more of the oligopeptides identified as SEQ ID No: 1 through SEQ ID NO: 111 and/or modifications to the invention and/or other peptidomimetics for the prevention or therapy of infectious diseases.

In another aspect of the invention, the use of one or more of the oligopeptides identified as SEQ ID No: 1 through SEQ ID NO: 111 and/or modifications to the invention and/or other peptidomimetics for the prevention or therapy of diseases that may turn out to be caused or related to African Swine virus.

In yet another aspect of the invention, the preventive and therapeutic use of one or more of the oligopeptides identified as SEQ ID No: 1 through SEQ ID NO: 111 and/or modifications to the invention and/or peptidomimetics according to claim 1 to 10 where the oligopeptides are coupled to haptens to enhance immune response and thereby therapeutic efficacy.

In still yet another aspect of the invention, the use of one or more of the oligopeptides and/or modifications thereof identified as SEQ ID No: 1 through SEQ ID NO: 111 and/or other peptidomimetics of the invention for the production of specific antibodies for the diagnosis of a disease involving African Swine virus or the clinical monitoring of the progression or regression of this disease.

In one preferred embodiment of the invention, the use of one or more of the oligopeptides identified as SEQ ID No: 1 through SEQ ID NO: 111 and/or modifications to the invention and/or other peptidomimetics for the production of specific antibodies for the diagnosis or the clinical monitoring of the progression or regression of immune deficiencies.

Figure 1:
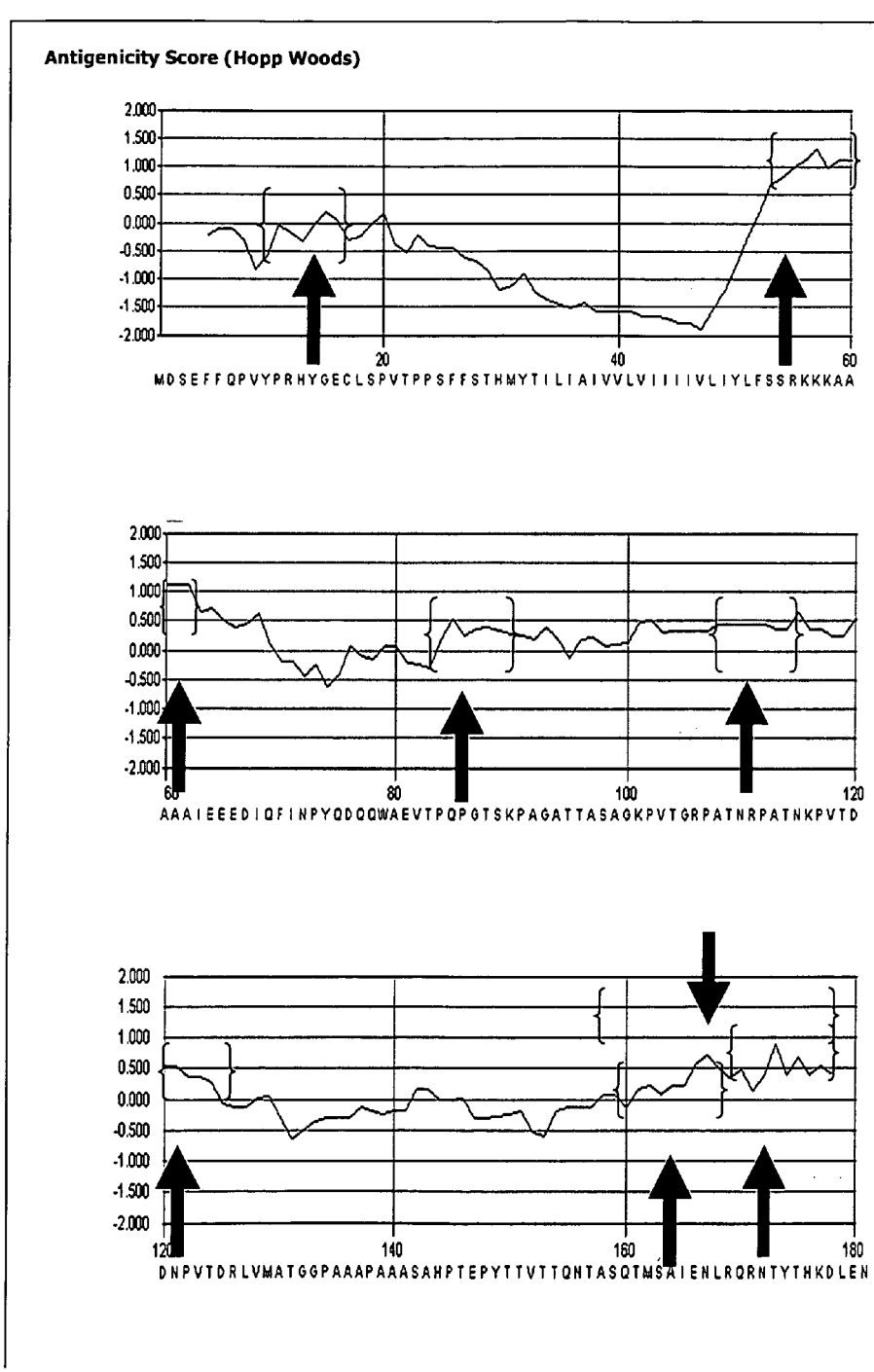
FIG. 1 shows the antigenicity scores derived from and according to the Hopp-Woods hydrophylicity algorithm for the protein p54, a 183 amino acid long structural protein of the African Swine virus. Since p54 is involved in the pathogenesis of African Swine fever (2), interrupting this pathogenicity-mediating pathway will lead to a decrease or a complete block of infection by this virus.

The relative peaks of this algorithm, defined as amino acid sequence regions of either high hydrophilic characteristics or sequence regions of higher hydrophilic characteristics in relation to adjacent amino acid sequences or in comparison to hydrophobic regions of the protein, represent the likely candidate sequence regions (oligopeptides) serving as epitopes (antigens) for antibody formation. Moreover these defined oligopeptide sequences represent the likely region by which a protein interacts with other proteins and/or biological compounds in an organism, including those interactions that mediate infection or other forms of pathogenicity.

Producing synthetic oligopeptides, corresponding to these algorithm maxima allows the development of preventive and therapeutic agents to control African Swine Fever virus infections. The relative peaks of the Hopp-Woods algorithm for the p54 protein of the African Swine Fever virus are marked by arrows and they are SEQ ID No. 112, SEQ ID No. 113, SEQ ID No. 114, SEQ ID No. 115, SEQ ID No. 116, SEQ ID No. 117, SEQ ID No. 118, SEQ ID No. 119, SEQ ID No. 120. The synthetic oligopeptides for the other African Swine fever Virus proteins specified in this disclosure and the claims are selected in an analogous way.

DETAILED DESCRIPTION OF THE INVENTION

The African Swine virus is a particular virus the pathogenicity of which is largely determined by targeting the immune system of the host and disabling it.

Despite the DNA sequence of African Swine virus having been determined (3), there is currently no effective vaccine available to control African Swine fever as documented in the United Nations Food and Agricultural Organization's field handbook on this disease (4)

The present invention describes the identification and production of preventive and therapeutic agents, which—among others—can be used as vaccines against African Swine fever with the following specific steps being taken:

1. The identification of structural proteins and/or pathogenicity-mediating proteins and/or any other protein from the African Swine virus.
2. The analysis of the amino acid sequence of these proteins using specific algorithms allowing the determination of relative hydrophilic and/or polarity and/or charge and/or surface probability peaks and/or any other method allowing the determination of potential epitopes within these African Swine fever virus proteins.
3. The production of synthetic oligopeptides analogous to the epitope forming oligopeptides identified within the amino acid sequence of the African Swine fever virus proteins.
4. The modification of these synthetic oligopeptides to allow or improve antigencity and the formation of antibodies and/or to block pathogenicity of the African Swine fever virus in any other way by
   a. adding one or several predetermined amino acids to the selected oligopeptide sequence;
   b. subtracting one or several predetermined amino acids to the selected oligopeptide sequence;
   c. replacing one or several predetermined amino acids within the selected oligopeptide sequence;
   d. changing the linear topology of the selected oligopeptide to a cyclic topology;
   e. forming a linear chain of covalently bound repeats of the selected oligopeptide sequence;
   f. forming a cyclic chain of covalently bound repeats of the selected oligopeptide sequence;
   g. coupling an originally selected and/or modified oligopeptide to one or more haptens;
   h. to improve antigencity and enhance antibody formation in any other possible way;
   i. producing natural and/or synthetic peptidomimetics mimicking the three dimensional structure of the natural or modified oligopeptide.

5. To conduct in vitro and in vivo tests with the selected oligopeptides and/or peptidomimetics in order to establish their efficacy and efficiency as a therapeutic or diagnostic agents.
6. To identify those originally selected and/or modified synthetic oligopeptides and/or peptidomimetics for therapeutic or diagnostic use that
   a. display maximum and/or optimum ability to form antibodies against the African Swine virus as potential therapeutic vaccines;
   b. display maximum and/or optimum competitive inhibition of pathogenicity mediating pathways of the African Swine virus as potential therapeutic agents used for—but not limited to—acute therapeutic treatment of African Swine fever;
   c. display maximum and/or optimum antigenicity to raise antibodies for the development of tests to diagnose African Swine fever.
7. To use those originally selected and/or modified synthetic oligopeptides and/or peptidomimetics as therapeutic vaccines that display maximum and/or optimum ability to form antibodies against the African Swine virus.
8. To use those originally selected and/or modified synthetic oligopeptides and/or peptidomimetics as therapeutic vaccines that display maximum and/or optimum ability for competitive inhibition of pathogenicity mediating pathways of the African Swine virus as potential therapeutic agents used for—but not limited to—the acute therapeutic treatment of African Swine fever.
9. To use those originally selected and/or modified synthetic oligopeptides and/or peptidomimetics that display maximum and/or optimum antigenicity to be used in the development of diagnostic tests or screening procedures for the African Swine virus.

The current invention also describes the application of the current invention for the diagnosis and treatment of immune deficiency conditions in mammals.

The following are the characteristics of the African Swine Virus:
1. it targets the immune system of the host
2. it has the following morphological features, in particular it structurally and functionally impairs the lymph nodes and other integral parts of the immune system;
3. its hematological changes includes a significant decrease of CD4 and T-cell counts;
4. both viruses share similar clinical findings, namely lymph node swelling, increased susceptibility to infections, and others;
5. it has both an acute and chronic form of infectious states;
6. it is known to display a high frequency of alteration of their genetic sequence in order to escape the host defense system;
7. it is endemic in sub-Saharan Africa and few other regions.

While the African Swine virus has been primarily detected in pigs and certain other animals, antibodies against the African Swine virus have also been found in humans (5). The fact that there was no description of any finding of the African Swine virus in humans may thus be attributable to oversight or a lack of understanding for the significance of African Swine fever virus for the pathogenicity of immune deficiencies in humans.

Thus, the inventions described in this patent application can have far reaching implications not only for the control of African Swine fever but also for the control of other immunodeficiency diseases.

The main structural and/or pathogenicity mediating proteins of the African Swine virus are the following:

```
                                                (SEQ ID NO: 1)
Ser-Arg-Pro-Pro-Leu-Ser-Ser-Glu-Ala-Asn-Leu-Tyr-
Ala-Lys-Leu-Gln-Asp-His-Ile-Gln-Arg-Gln-Thr-Arg-
Pro-Phe-;

(SEQ ID NO: 2)
Gly-Asp-Lys-Asn-Pro-Val-Gln-His-Ile-Lys-Asp-Tyr-
His-Ile-Asp-Ser-;

(SEQ ID NO: 3)
Ser-Lys-Ala-Lys-Leu-Arg-Val-Ile-Glu-Gly-Ile-Ile-
Arg-Ala-;

(SEQ ID NO: 4)
Phe-Lys-Val-Asp-Thr-Lys-Gln-Pro-Ile-Glu-Asp-Ile-
Leu-Lys-Asp-Ile-Lys-Lys-Gln-Leu-Pro-Asp-Pro-Arg-
Ala-;

(SEQ ID NO: 5)
Ala-Glu-Lys-Gln-Glu-Thr-Val-Cys-Lys-Met-;

(SEQ ID NO: 6)
Gln-Glu-Phe-Ile-Asp-Leu-Gly-Gln-Asp-Lys-Leu-Ile-
Asp-Thr-;

(SEQ ID NO: 7)
Ala-Glu-Lys-Gln-Glu-Thr-Val-Cys-Lys-Met-Ile-Ala-
Asp-Ala-Ile-Asn-Gln-Glu-Phe-Ile-Asp-Leu-Gly-Gln-
Asp-Lys-Leu-Ile-Asp-Thr-Thr-Asp-Gly-Ala-Ala-Ser-
Ile-Cys-Arg-Gln-;

(SEQ ID NO: 8)
Leu-Arg-Ala-Glu-Tyr-Leu-Asp-Val-His-Gly-Ser-Ile-
Glu-Asn-Thr-Leu-Glu-Asn-Ile-Lys-Leu-;

(SEQ ID NO: 9)
Asn-Asp-Ala-Ile-Lys-Gln-Leu-His-Glu-Arg-Met-Val-;

(SEQ ID NO: 10)
Thr-Glu-Val-Thr-Lys-Ala-Ala-Pro-Asn-Glu-Glu-Val-;

(SEQ ID NO: 11)
Ile-Glu-Ala-Val-Tyr-Arg-Arg-Leu-Leu-Asn-Glu-Gln-
Asn-Leu-;

(SEQ ID NO: 12)
Thr-Gln-Lys-Glu-Leu-Asp-Lys-Leu-Gln-Thr-Asp-Glu-
Val-Asp-Ile-;

(SEQ ID NO: 13)
Leu-Cys-Asn-Leu-Gly-Ile-Ala-Ala-Ser-Val-Ala-Asn-
Lys-Ile-Asn-Lys-Ala-Leu-Gln-Lys-Val-Gly-Leu-Lys-
Val-Glu-Gln-Tyr-Leu-Gln-Ser-Lys-Asn-Trp-Ala-Glu-
Phe-Asp-Lys-Glu-Leu-Asp-Leu-Lys-Arg-Phe-Ser-Gly-
Leu-Val-Ser-Ala-Glu-Asn-Ile-Ala-Glu-Phe-Glu-Lys-
Ala-Val-Asn-Leu-Leu-Arg-Gln-Thr-Phe-Asn-Glu-Arg-
His-Lys-Ile-Leu-Glu-Asn-Ser-Cys-Ala-;

(SEQ ID NO: 14)
Asn-Lys-Ile-Asn-Lys-Ala-Leu-Gln-Lys-Val-Gly-Leu-
Lys-Val-;

(SEQ ID NO: 15)
Ser-Lys-Asn-Trp-Ala-Glu-Phe-Asp-Lys-Glu-Leu-Asp-
Leu-Lys-Arg-Phe-;

(SEQ ID NO: 16)
Ala-Glu-Asn-Ile-Ala-Glu-Phe-Glu-Lys-Ala-Val-Asn-
Leu-Leu-Arg-Gln-Thr-Phe-Asn-Glu-Arg-His-Lys-Ile-
Leu-Glu-Asn-;

(SEQ ID NO: 17)
Ala-Lys-Lys-Gly-Gly-Asp-Glu-Glu-Lys-Thr-;

(SEQ ID NO: 18)
Pro-Leu-Asp-Arg-Arg-Ile-Glu-Ala-Gln-Arg-Leu-Asp-
Arg-Lys-His-Ile-;
```

-continued (SEQ ID NO: 19)
Ala-Lys-Lys-Gly-Gly-Asp-Glu-Glu-Lys-Thr-Pro-Leu-
Asp-Arg-Arg-Ile-Glu-Ala-Gln-Arg-Leu-Asp-Arg-Lys-
His-Glu-;

(SEQ ID NO: 20)
Asn-Asp-Phe-Leu-Glu-Asn-Val-Lys-Lys-Ile-Gly-Ile-
Lys-Leu-Val-Lys-Glu-Ile-;

(SEQ ID NO: 21)
Thr-Arg-Leu-Arg-Asp-Ala-Leu-Ser-Arg-Ile-Asn-Asp-
Met-;

(SEQ ID NO: 22)
Ala-Arg-Glu-Glu-Arg-Glu-Thr-Phe-;

(SEQ ID NO: 23)
Val-Lys-Asn-Val-Leu-Glu-Glu-Gln-Ser-Lys-Ile-Asp-
Pro-Asn-Phe-Lys-Asn-;

(SEQ ID NO: 24)
Tyr-Asp-Ser-Cys-Ser-Arg-Leu-Leu-Gln-Ile-Ile-Asp-
Phe-Tyr-Thr-Asp-Ile-Val-Gln-Lys-Lys-Tyr-Gly-Gly-
Gly-Glu-Asp-Cys-Glu-Cys-Thr-Arg-Val-;

(SEQ ID NO: 25)
Tyr-Asp-Ser-Cys-Ser-Arg-Leu-Leu-Gln-Ile-Ile-Asp-
Phe-Tyr-Thr-Asp-Ile-Val-Gln-Lys-Lys-Tyr-Gly-Gly-
Gly-Glu-Asp-Cys-Glu-;

(SEQ ID NO: 26)
Val-Gln-Lys-Lys-Tyr-Gly-Gly-Gly-Glu-Asp-Cys-Glu-
Cys-Thr-Arg-Val-;

(SEQ ID NO: 27)
Val-Glu-Glu-Leu-Gly-Leu-Ser-Lys-Ala-Ala-Arg-Ser-
Gln-Val-Asp-Leu-Asn-Gln-Ala-Ile-Asn-Thr-Phe-Met-
Tyr-Tyr-Tyr-Tyr-Val-Ala-Gln-Ile-Tyr-Ser-Asn-Leu-
Thr-His-Asn-Lys-Gln-Glu-Phe-Gln-Ser-Tyr-Glu-Glu-
Asn-;

(SEQ ID NO: 28)
Thr-His-Asn-Lys-Gln-Glu-Phe-Gln-Ser-Tyr-Glu-Glu-
Asn-;

(SEQ ID NO: 29)
Met-Gln-Leu-Asp-Thr-Glu-Lys-Asn-Ala-Arg-Ile-Asn-
Ser-Pro-Ala-Val-Asp-Leu-Ala-Arg-Gly-;

(SEQ ID NO: 30)
Ala-Gln-Glu-Ala-Asp-Trp-Lys-Ala-Ala-Val-Ser-Ala-
Ile-Glu-Leu-Glu-Tyr-Asp-Val-Lys-Arg-Arg-Phe-Tyr-
Arg-Ala-Leu-Glu-Gly-Leu-Asp-Leu-;

(SEQ ID NO: 31)
Leu-Lys-Asn-Ile-Thr-Lys-Thr-Phe-Val-Asn-Asn-Ile-
Asp-Ser-;

(SEQ ID NO: 32)
Leu-Asp-Gly-Val-Arg-Ile-Ile-Gly-Arg-Trp-Phe-Thr-
Glu-Ala-Thr-Gly-Asp-Thr-;

(SEQ ID NO: 33)
Ala-Glu-Ile-Gln-Gln-Gly-Arg-Ser-Val-Gly-Thr-Leu-
Arg-Pro-Val-Arg-Ala-Ser-Gln-Ala-Lys-Asn-Ile-Arg-
Asp-Leu-;

(SEQ ID NO: 34)
Ala-Arg-Ile-Gly-Asp-Met-Leu-Gly-Gly-Glu-Glu-Leu-
Arg-Gln-Met-;

(SEQ ID NO: 35)
Leu-Lys-Asn-Leu-Asn-Gln-Ser-Glu-Ile-Gly-Gly-Gln-
Arg-Val-Ala-Leu-Ala-Arg-Thr-Pro-Glu-Glu-Ala-Ala-
Gln-Arg-Val-;

(SEQ ID NO: 36)
Asn-Asp-Ala-Leu-Ser-Thr-Arg-Trp-Glu-Thr-Glu-Asp-
Val-;

(SEQ ID NO: 37)
Tyr-Asp-Met-Phe-Glu-Arg-Pro-Glu-Pro-Val-Tyr-Lys-
Leu-;

(SEQ ID NO: 38)
Ala-Asp-Glu-Leu-Glu-Pro-Glu-Val-Ile-Pro-Glu-Ala-
Ala-Glu-Leu-Tyr-Phe-Arg-Leu-Pro-Arg-Leu-;

(SEQ ID NO: 39)
Phe-Arg-Leu-Pro-Arg-Leu-Ala-Glu-Phe-Tyr-Gln-Lys-
Leu-;

(SEQ ID NO: 40)
Met-Arg-Pro-Ile-Glu-Leu-Ile-Asn-Ile-Gly-Asp-Tyr-
Ser-Glu-Thr-Glu-Ile-Arg-Gln-Leu-Ile-Lys-Glu-Ile-;

(SEQ ID NO: 41)
Leu-Glu-Tyr-Gly-Glu-Gln-Glu-Ala-Thr-Lys-Lys-Ala-
Leu-Ile-His-Phe-Val-Asn-Glu-Ile-;

(SEQ ID NO: 42)
Asn-Arg-Arg-Phe-Gly-Val-Ile-Thr-Arg-Thr-Glu-Trp-
Glu-Lys-Phe-Gln-Arg-Ile-;

(SEQ ID NO: 43)
Gln-Arg-Ile-Val-Gln-Glu-Ala-Arg-Thr-Met-Asn-Asp-
Phe-Gly-;

(SEQ ID NO: 44)
Ser-Gln-Trp-Asp-Leu-Val-Gln-Lys-Phe-Arg-Lys-Gln-
Leu-;

(SEQ ID NO: 45)
Gln-Lys-Phe-Arg-Lys-Gln-Leu-Ser-Glu-Met-Phe-Glu-
Asp-Pro-Ser-;

(SEQ ID NO: 46)
Gln-Gln-Glu-Leu-Gly-Lys-Val-Ser-Tyr-Gln-Glu-Leu-
Ile-Arg-Gln-;

(SEQ ID NO: 47)
Ile-Asn-Glu-Leu-Lys-Lys-Glu-His-Thr-Asp-Lys-Ile-
Gln-Ile-Val-Ser-Lys-Leu-;

(SEQ ID NO: 48)
Leu-Lys-Lys-Glu-His-Thr-Asp-Lys-Ile-Gln-Ile-Val-
Ser-Lys-Leu-Ile-Gln-Gly-Ser-Glu-Ser-Leu-Ala-Asp-
Thr-Asp-Val-Asn-Lys-Ile-;

(SEQ ID NO: 49)
Phe-Arg-Asn-Asn-Ile-Lys-Gly-Leu-Asp-Leu-Asp-Thr-
Ile-Gln-Lys-Ser-;

(SEQ ID NO: 50)
Ile-Glu-Trp-Leu-Arg-Glu-Thr-Gln-Ala-Ala-Asn-Val-
Asn-Arg-Ala-;

(SEQ ID NO: 51)
Ile-Asp-Trp-Leu-Gly-Arg-Lys-His-Gly-Ala-Ile-Ser-
Glu-Ile-;

(SEQ ID NO: 52)
Ile-Arg-Asn-Pro-Gly-Leu-Val-Val-Lys-Glu-Asn-Asp-
Val-Arg-Leu-Ser-Arg-Val-;

(SEQ ID NO: 53)
Ala-Glu-Gln-Glu-Leu-Ala-Ala-Arg-Tyr-Leu-Val-Asp-
Asn-Gln-Arg-Ile-;

(SEQ ID NO: 54)
Phe-Asn-Lys-Met-Val-Gln-Val-Arg-Phe-Pro-Glu-Thr-;

(SEQ ID NO: 55)
Ile-Asp-Ser-Leu-Met-Ala-Asp-Thr-Lys-Tyr-Phe-Leu-
Asn-Leu-Leu-Arg-Pro-His-Ile-Asp-Lys-Asn-;

(SEQ ID NO: 56)
Leu-Glu-Glu-His-Leu-Ile-Asp-Lys-Leu-Ile-Lys-Pro-
Pro-Thr-Asp-Ala-;

-continued (SEQ ID NO: 57)
Leu-Gln-Leu-Arg-Gly-Gly-Val-Gln-Arg-Arg-Asp-Ala-;

(SEQ ID NO: 58)
Ser-Glu-Arg-Phe-Glu-Gln-Tyr-Gly-Arg-Val-;

(SEQ ID NO: 59)
Leu-Gln-Leu-Arg-Gly-Gly-Val-Gln-Arg-Arg-Asp-Ala-
Ala-Asn-Ile-Gln-Ile-Asn-Asn-Asn-Pro-Gln-Pro-Ser-
Glu-Arg-Phe-Glu-Gln-Tyr-Gly-Arg-Val-;

(SEQ ID NO: 60)
Ile-Arg-Thr-Asn-Asn-Ala-Gln-Glu-Glu-Asn-Thr-;

(SEQ ID NO: 61)
Leu-Arg-Arg-Tyr-Arg-Leu-Tyr-Gly-Ser-Asp-Tyr-;

(SEQ ID NO: 62)
Ala-Arg-Phe-Tyr-Asp-Ala-Pro-Ser-Gly-Lys-Ile-;

(SEQ ID NO: 63)
Met-Glu-Leu-Gly-Tyr-Thr-His-Pro-Asp-Leu-Ala-Arg-
Asp-Asn-Ile-Ala-Phe-Gly-His-Arg-Gly-Asp-Pro-Thr-
Glu-Gln-Ser-;

(SEQ ID NO: 64)
Leu-Gln-Arg-Leu-Ile-Lys-Asp-Thr-Asn-Arg-Gln-Gly-;

(SEQ ID NO: 65)
Thr-Glu-Ile-Pro-Ile-Tyr-Leu-Lys-Glu-Asn-Tyr-Arg-
Ala-;

(SEQ ID NO: 66)
Leu-Gln-Arg-Leu-Ile-Lys-Asp-Thr-Asn-Arg-Gln-Gly-
Leu-Ser-Gln-His-Leu-Ile-Ser-Thr-Leu-Thr-Glu-Ile-
Pro-Ile-Tyr-Leu-Lys-Glu-Asn-Tyr-Arg-Ala-;

(SEQ ID NO: 67)
Ser-Asp-Val-Val-Arg-Lys-Arg-Leu-Val-Ala-Val-Ile-
Asp-Gly-Ile-Ile-Arg-Gly-;

(SEQ ID NO: 68)
Tyr-Leu-Glu-Thr-Glu-Glu-His-Phe-Ile-Gln-Asn-Tyr-
Met-Ser-Arg-Tyr-Asn-Lys-Glu-Pro-;

(SEQ ID NO: 69)
Tyr-Leu-Arg-Asp-Leu-Arg-Ile-Glu-Asn-Asn-Glu-Val-
Tyr-Asp-Pro-Leu-;

(SEQ ID NO: 70)
Leu-Glu-Ser-Gly-Ser-Pro-Glu-Phe-Lys-Leu-Leu-Tyr-
Gly-Thr-Arg-Lys-Leu-;

(SEQ ID NO: 71)
Met-Lys-Asn-Tyr-Asn-Glu-Thr-Val-Val-Ala-Arg-Glu-
Gln-Ile-Thr-Pro-Thr-Arg-Phe-Glu-His-;

(SEQ ID NO: 72)
Ile-Ser-Glu-Asn-Arg-Asp-Asp-Lys-Pro-Ile-;

(SEQ ID NO: 73)
Leu-Arg-Lys-Thr-Leu-Gln-Asp-Val-Ile-Ser-Phe-Val-
Glu-Ser-Ser-Tyr-Gln-Glu-Glu-Gln-Ile-Asn-His-Ile-
His-Lys-Ile-;

(SEQ ID NO: 74)
Pro-Lys-Gly-Gln-Thr-Arg-Thr-Leu-Gly-Ser-Asn-Arg-
Glu-Arg-Glu-Arg-Ile-;

(SEQ ID NO: 75)
Tyr-Asp-Tyr-Ser-Phe-Glu-Glu-Ile-Ala-Cys-Leu-Met-
Tyr-Gly-Ile-Ser-Ala-Glu-Lys-Val-Arg-Ser-;

(SEQ ID NO: 76)
Pro-Asp-Ile-Ala-Glu-Val-Leu-Asn-Ile-Pro-Asn-Arg-
Pro-Pro-Met-Asn-Thr-Arg-Glu-Phe-Met-Leu-Lys-Leu-;

(SEQ ID NO: 77)
Met-Ser-Arg-Ile-Phe-Arg-Gly-Asp-Asn-Ala-Leu-Asn-
Met-Gly-Arg-Pro-Lys-Phe-Leu-Ser-Asp-Gln-Ile-Phe-
Asn-Lys-Val-;

(SEQ ID NO: 78)
Ile-Gln-Arg-Gly-Arg-Glu-Gln-Trp-Gly-;

(SEQ ID NO: 79)
Glu-Tyr-Ile-Asn-Gln-Ala-Leu-His-Glu-Leu-Val-Arg-
Thr-Ile-Arg-Ile-Pro-Gln-Lys-Leu-Arg-Val-Leu-Arg-
Asn-;

(SEQ ID NO: 80)
Ile-Arg-Glu-Gln-Leu-Val-Ser-Met-Arg-Arg-Glu-Val-
Glu-Asn-Met-Ile-Gln-Thr-Pro-Glu-Ile-Gln-Asn-Asn-
Pro-Thr-Pro-;

(SEQ ID NO: 81)
Thr-Gln-Gln-Tyr-Arg-Ala-Arg-Val-Asp-Thr-;

(SEQ ID NO: 82)
His-Pro-Arg-Gln-Ile-Leu-Gln-Thr-Asp-Asp-Glu-Ala-;

(SEQ ID NO: 83)
Thr-Asp-Leu-Ala-Asn-Asp-Leu-Arg-Thr-Phe-Leu-Glu-
Thr-Leu-Glu-Arg-Tyr-;

(SEQ ID NO: 84)
Gly-Arg-Val-Ala-Arg-Ala-Pro-Val-Arg-Met-Ala-Pro-
Arg-Asp-Met-Arg-His-Pro-Ile-;

(SEQ ID NO: 85)
Thr-Asp-Leu-Ala-Asn-Asp-Leu-Arg-Thr-Phe-Leu-Glu-
Thr-Leu-Glu-Arg-Tyr-Val-Phe-Asn-Val-Pro-Arg-Trp-
Leu-Gly-Pro-Ser-Thr-Gly-Arg-Val-Ala-Arg-Ala-Pro-
Val-Arg-Met-Ala-Pro-Arg-Asp-Met-Arg-His-Pro-Ile-;

(SEQ ID NO: 86)
Thr-Glu-Gln-Asn-Arg-Glu-Glu-Gly-Pro-;

(SEQ ID NO: 87)
Thr-Glu-Gln-Asn-Arg-Glu-Glu-Gly-Pro-Trp-Ser-Ile-
Val-Lys-Gln-Val-Gly-Val-Gly-Ile-Gln-Lys-Pro-Thr-
Leu-Val-Gln-Ile-Gly-Lys-Asp-Arg-Phe-Asp-Thr-Arg-
Leu-;

(SEQ ID NO: 88)
Gly-Lys-Asp-Arg-Phe-Asp-Thr-Arg-Leu-;

(SEQ ID NO: 89)
Ile-Gln-Arg-Leu-Leu-Arg-Leu-Arg-Leu-Asn-Leu-Glu-
Leu-Ser-Gln-Phe-Arg-Asn-;

(SEQ ID NO: 90)
Val-Gln-Ile-Gly-Lys-Asp-Arg-Phe-Asp-Thr-Arg-Leu-
Ile-Arg-Asn-;

(SEQ ID NO: 91)
Ile-Gln-Arg-Leu-Leu-Arg-Leu-Arg-Leu-Asn-Leu-Glu-
Leu-Ser-Gln-Phe-Arg-Asn-;

(SEQ ID NO: 92)
Ser-Glu-Thr-Phe-Ser-Asp-Lys-Gln-Tyr-Asp-Ser-Asp-
Ile-Arg-Ile-;

(SEQ ID NO: 93)
Trp-Glu-Ser-Asp-Leu-Pro-Arg-His-Asn-Arg-Tyr-Ser-
Asp-Asn-;

(SEQ ID NO: 94)
Asn-Glu-Tyr-Thr-Asn-Ser-Pro-Glu-Lys-Ala-Glu-Lys-
Gly-Leu-Gln-Leu-Ser-Asp-Leu-Arg-Asn-;

(SEQ ID NO: 95)
Gln-His-Lys-Asn-Ile-Gly-Tyr-Gly-Asp-Ala-Gln-Asp-
Leu-Glu-Pro-Tyr-;

-continued (SEQ ID NO: 96)
Gly-Asp-Ala-Gln-Asp-Leu-Glu-Pro-Tyr-Ser-Ser-Ile-
Pro-Lys-Asn-Lys-Leu-;

(SEQ ID NO: 97)
Thr-Glu-Asn-Leu-Ile-Arg-Arg-Asn-Val-Val-Arg-Thr-
Glu-Lys-Lys-Thr-;

(SEQ ID NO: 98)
Thr-Arg-Phe-Ser-Glu-His-Thr-Lys-Phe-;

(SEQ ID NO: 99)
Tyr-Glu-Asp-Ile-Pro-Lys-Leu-Lys-Thr-Lys-Gly-Thr-
Ile-Lys-His-Glu-Gln-His-Leu-;

(SEQ ID NO: 100)
Val-Glu-Lys-Gly-Ile-Ala-Gly-Arg-Gly-;

(SEQ ID NO: 101)
Val-Lys-Pro-Asn-Ile-Glu-Gln-Glu-Leu-Ile-Lys-Ser-;

(SEQ ID NO: 102)
Val-Glu-Lys-Gly-Ile-Ala-Gly-Arg-Gly-Ile-Pro-Leu-
Gly-Asn-Pro-His-Val-Lys-Pro-Asn-Ile-Glu-Gln-Glu-
Leu-Ile-Lys-Ser-;

(SEQ ID NO: 103)
Pro-Lys-Asp-Ser-Gln-His-Gly-Arg-Glu-Tyr-Gln-Glu-
Phe-Ser-Ala-Asn-Arg-His;

(SEQ ID NO: 104)
Ile-Lys-Pro-Gln-Ile-Leu-Glu-Asp-Ile-;

(SEQ ID NO: 105)
Ser-Lys-Arg-Asn-Ser-Gly-Gln-Ala-Glu-Tyr-Phe-Asp-
Thr-Ser-Lys-Gln-;

(SEQ ID NO: 106)
Gly-Asp-Ser-Lys-Leu-Asp-Ser-Thr-Phe-Pro-Lys-Asp-;

(SEQ ID NO: 107)
Ala-Glu-Lys-Asp-His-Ser-Leu-Arg-Gly-Asp-Asn-;

(SEQ ID NO: 108)
Ser-Ala-Glu-Lys-Asp-His-Ser-Leu-Arg-Gly-Asp-Asn-
Ser-Ala-Cys-Cys-Ile-Ser-Asn-Tyr-Ile-Pro-Lys-Tyr-
Thr-Gly-Gly-Ile-Gly-Asp-Ser-Lys-Leu-Asp-Ser-Thr-
Phe-Pro-Lys-Asp-Phe-Asn-Ala-Ser-Ser-Val-Pro-Leu-
Thr-Ser-Ala-Glu-Lys-Asp-His-Ser-Leu-Arg-Gly-Asp-
Asn-Ser-Ala-Cys-Cys-Ile-;

(SEQ ID NO: 109)
Gly-Asp-Ser-Lys-Leu-Asp-Ser-Thr-Phe-Pro-Lys-Asp-
Phe-;

(SEQ ID NO: 110)
Ala-Glu-Lys-Asp-His-Ser-Leu-Arg-Gly-Asp-Asn-;

(SEQ ID NO: 111)
Gly-Asp-Ser-Lys-Leu-Asp-Ser-Thr-Phe-Pro-Lys-Asp-
Phe-Asn-Ala-Ser-Ser-Val-Pro-Leu-Thr-Ser-Ala-Glu-
Lys-Asp-His-Ser-Leu-Arg-Gly-Asp-Asn-.

REFERENCES CITED

1. Duncan R A et al. Idiopathic CD4+ T-lymphocytopenia—four patients with opportunistic infections and no evidence of HIV infection. N Engl J Med. 1993; 328(6): 393-8.
2. Rodriguez F et al. Characterization and molecular basis of heterogeneity of the African Swine Fever virus envelope protein p54. J Virol 1994; 68 (11): 7244-7252.
3. Yanez R J et al. Analysis of the complete nucleotide sequence of African Swine Fever virus. Virology 1995; 208: 249-278.
4. Recognizing African Swine Fever, A Field Manual, UN Food and Agricultural Organization, ISBN 92-5-104471-6
5. Hess W R. African Swine Fever: A Reassessment. Advances in Veterinary Science and Comparative Medicine Vol. 25. Cornelius C E, Simpson C F eds. Academic Press, New York, 1981:39-69.

What is claimed is:

1. An isolated oligopeptide according to SEQ ID NO: 1.

2. The oligopeptide according to claim 1, wherein the sequence identified as SEQ ID No: 1 is modified by using cyclic oligopeptide topology instead of linear oligopeptide topology.

* * * * *